United States Patent [19]
Jacobs et al.

[11] Patent Number: 4,966,167
[45] Date of Patent: Oct. 30, 1990

[54] SURGICAL DRAPE FOR APPLYING TRACTION

[75] Inventors: Randall W. Jacobs, Santa Ana; Robert H. Peterson, Ranco Santa Margarita, both of Calif.

[73] Assignee: Baxter International Inc., Deerfield, Ill.

[21] Appl. No.: 296,970

[22] Filed: Jan. 13, 1989

[51] Int. Cl.$^5$ .............................................. A61B 19/00
[52] U.S. Cl. ..................................... 128/849; 128/856
[58] Field of Search ...................... 128/83, 84 R, 87 R, 128/87 C, 69, 77, 849, 846, 856

[56] References Cited

U.S. PATENT DOCUMENTS

| | | | |
|---|---|---|---|
| 2,783,758 | 3/1957 | Trott | 128/84 R |
| 3,390,675 | 7/1968 | Gianestras | 128/84 R |
| 3,872,861 | 3/1975 | Tamny et al. | 128/84 R |
| 3,957,041 | 5/1976 | Wilder | 128/94 |
| 4,089,064 | 5/1978 | Chandler, Jr. | 2/2 |
| 4,583,534 | 4/1986 | Woods et al. | 128/80 R |
| 4,679,552 | 7/1987 | Caspari | 128/856 |
| 4,777,859 | 10/1988 | Plummer, Jr. | 87/7 |

Primary Examiner—Robert A. Hafer
Assistant Examiner—Lynda M. Cofsky
Attorney, Agent, or Firm—June M. Bostich; Frank Uxa

[57] ABSTRACT

An apparatus useful for applying a traction force from a traction force system to a limb of a patient comprising:

an elongated tubular member having an open first end and an opposing second end, sized and adapted to receive a substantial portion of a limb of a patient through the first open end, and being constructed so as to contract around at least a portion of the received limb upon the application of a traction force on the second end;

an elongated hollow element having an open end and a sidewall which is microbially impermeable, sized and adapted to receive the received limb through the open end, at least a portion of the elongated hollow element substantially surrounds or is substantially surrounded by the elongated tubular member; and an attachment assembly secured to the elongated tubular member and acting to connect the elongated tubular member to the traction force system.

35 Claims, 2 Drawing Sheets

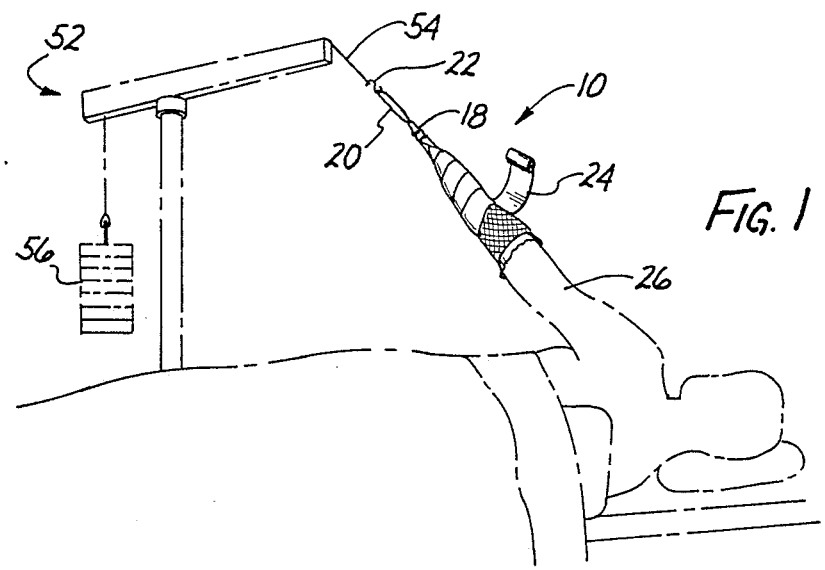
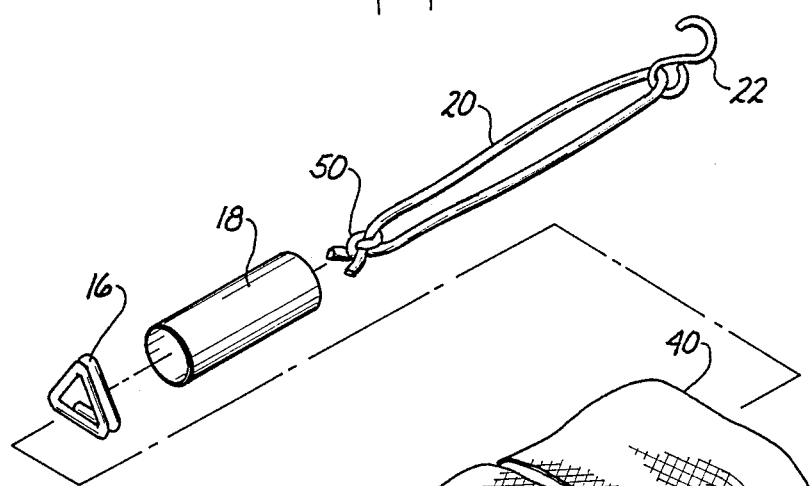
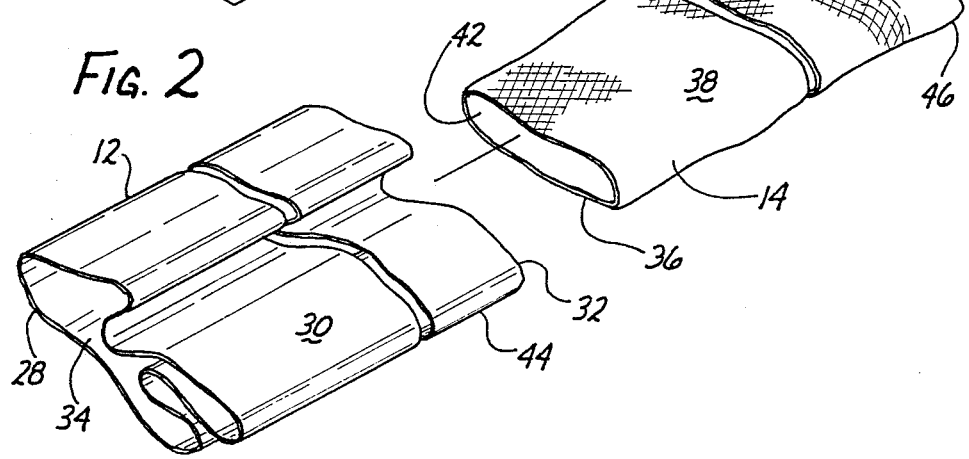
FIG. 1
FIG. 2

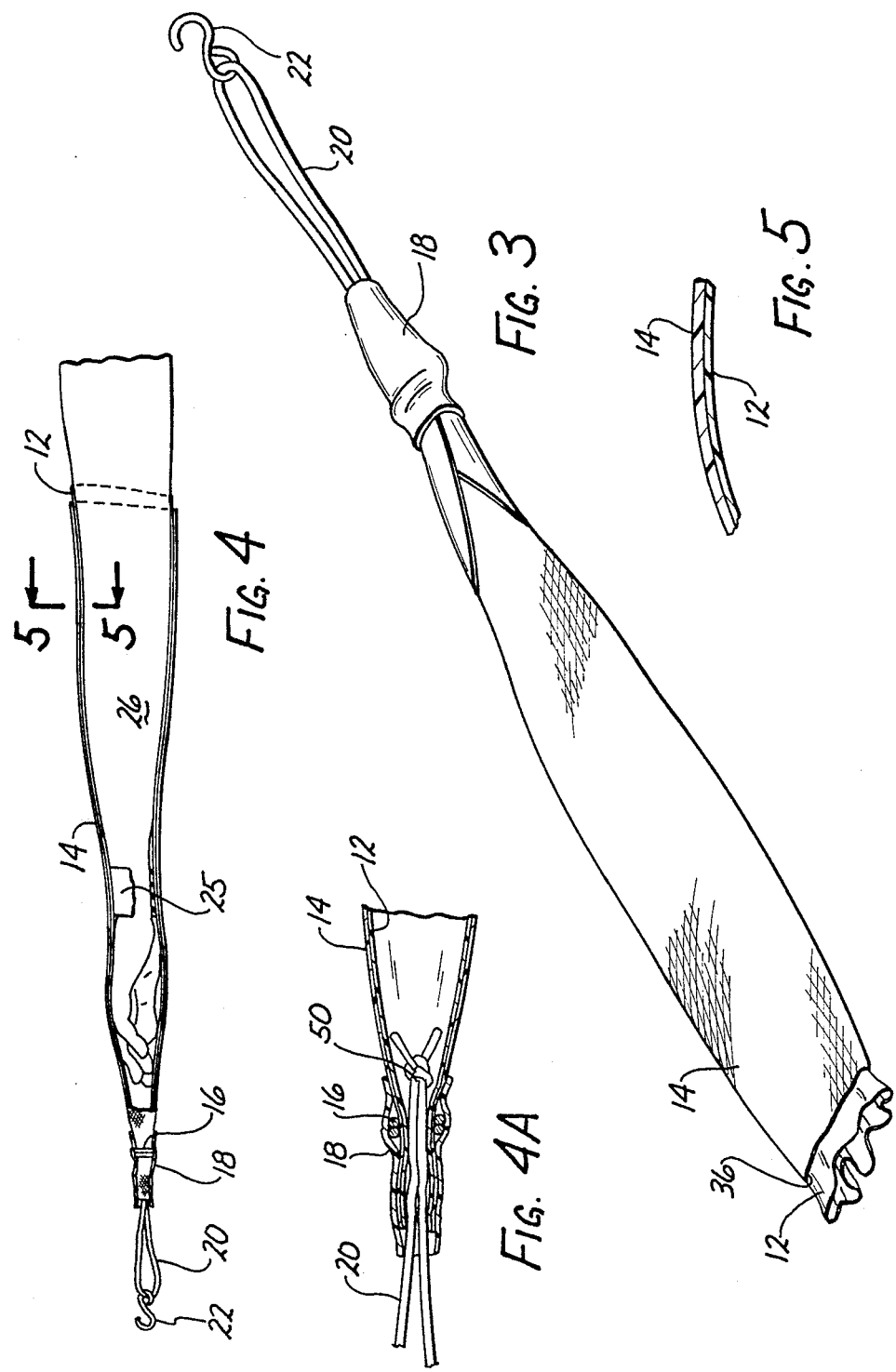

SURGICAL DRAPE FOR APPLYING TRACTION

BACKGROUND OF THE INVENTION

This invention relates to an apparatus for applying traction to a limb of a patient. More particularly, the invention relates to a protective covering or drape for use, e.g., during surgery or the like, on the patient's limb to apply traction.

During surgery, e.g., arthroscopic surgery, or the like, it may be necessary to apply traction to a limb of the patient. Various systems for applying such traction have been suggested and used. Certain of these prior systems have focused all of the traction force on one relatively small area of the limb, with the result that the small area becomes injured. For example, a system for applying traction to an arm may apply the force to the wrist, and cause a wrist injury. Additionally, the traction force might not be evenly applied, which can also result in injury to the limb.

Another concern regarding surgical or the like procedures is that of maintaining the sterile field. Thus, it is important that the limb being placed in traction does not contaminate the sterile field, e.g., within the operating room, and is not contaminated by microbes which may exist in the operating room. It is advantageous to protect or isolate the limb under traction with a surgical drape which is microbially impermeable.

Casperi U.S. Pat. No. 4,679,552 discloses a surgical drape for a limb in traction. A two layer sleeve is disclosed with an inner layer of soft textile material and an outer layer of moisture impermeable sheet material, such as a thin sheet of latex. Traction pads are stitched to the interior of the two layer sleeve. The traction force is applied to these traction pads which contact the limb so that the force is distributed along the contact area between the traction pads and the limb. Although Casperi does reduce the concentration of traction force to some extent, this force is not uniformly distributed around the periphery of the limb. Also, although water impermeable latex is used, it is repeatedly stitched through in fabricating the surgical drape. Such stitches or punctures reduces the usefulness of the latex as a sterile barrier.

A number of medical devices have been suggested using a component of a contractible material and construction such as that used in what is commonly known as a "Chinese Finger Trap". Such component is adapted to contract about, and often grip at least to some extent, an object inserted in the component whenever an attempt is made to withdraw the object therefrom. See, for example, Trott U.S. Pat. No. 2,783,758; Giannestras U.S. Pat. No. 3,390,675 and Tammy, et. al. U.S. Pat. No. 3,872,861. However, each of these patents involved holding only a thumb, toe or finger, so that even distribution of traction forces over a relatively large area was not an issue. Also, none of these patents are concerned with maintaining a sterile barrier.

SUMMARY OF THE INVENTION

A new apparatus, e.g., a protective surgical drape, useful for applying traction force to a limb of a patient has been discovered. The present system provides for applying an even, substantially uniformly distributed traction force to a limb, such as an arm or leg, of a patient, for example, who is undergoing surgery or a like procedure. The traction force is substantially evenly distributed over a relatively large area of the limb, thereby reducing the chances of injury. In addition, the apparatus includes a sterile barrier which keeps the protected limb from contaminating and/or being contaminated by the surrounding environment. In certain embodiments the sterile barrier itself is protected from being compromised. All this and more is accomplished employing a relatively simple and straight forward structure. Moreover, the system is easy to use, is relatively independent of surgical technique and, because of the substantially uniform distribution of the traction force, requires little or no rotational orientation.

In one broad aspect, the present apparatus includes an elongated tubular member, an elongated hollow element and an attachment means. The tubular member has an open first end and an opposing second end, and is sized and adapted to receive a substantial portion of a limb of a patient through the open first end. This tubular member is constructed so as to contract around at least a portion of the received limb, i.e., that portion of the limb received by the tubular member, upon the application of a traction or pulling force on the second end. In one embodiment, the tubular member is constructed and/or configured analogously to the prior "Chinese Finger Trap" devices noted above.

The elongated hollow element has an open end and a sidewall which is microbially impermeable. This element is sized and adapted to receive the received limb through its open end. At least a portion of the elongated hollow element substantially surrounds or is substantially surrounded by the tubular member.

The attachment means is secured to the tubular member and acts to connect the tubular member to the traction force system, e.g., comprising weights, which generates the traction force.

A bandage means, e.g., a conventional elastic bandage such as a self-adhering wrap sold under the trademark "Coban" by the 3M Company, is preferably included and acts to secure the position of the received limb relative to the tubular member. Thus, for example, the bandage is wrapped around the tubular member or the hollow element to more securely hold the received limb in place, in its received position.

The tubular member is preferably seamless. Thus, this member is preferably cut to the desired length from seamless tube stock. The cut ends may be sealed, e.g., with adhesives and/or heat, to maintain the integrity of the tubular element. The proximal end, i.e., the first open end, of the tubular member can be sealed with this end and the proximal portion of the members sidewall in an expanded state, while the distal end, i.e., the second end, can be sealed with the distal end and the distal portion of the member's sidewall in a contracted state. The tubular member preferably includes a porous sidewall. In one embodiment, the tubular member is preferably made of a braided material, more preferably braided monofilament fibers. The use of monofilament fibers provides a certain advantageous "memory" or stiffness to the tubular member. This stiffness makes placing the limb in the member easier. On the other hand, a stiff tubular member has a relatively limited ability to contract around the received limb. Thus, when monofilament fibers are used in the tubular member, it may be necessary to use the bandage means to hold the received limb in place.

Any suitable material may be used to fabricate the tubular member. This member is preferably made of synthetic materials, more-preferably synthetic polymeric materials. One particularly useful class of tubular member materials are the polyesters, especially polyesters sold under the trademark "Dacron" by DuPont. Expandable monofilament sleeving sold by Natvar and a self-fitting protective oversleeve sold under the trademark "Expando Tightweave" by Bentley Harris, or similar materials may be used to fabricate the tubular member.

The elongated hollow element is situated so that at least a portion of this element substantially surrounds or is substantially surrounded by the tubular member. Preferably, at least a portion of the hollow element is substantially surrounded by the elongated tubular member. In this configuration, the tubular member, which preferably has increased tear strength relative to the hollow element, helps protect the hollow element from tears, accidental scalpel cuts and the like. In so doing, tubular member helps maintain the integrity of the sterile barrier. The hollow element preferably extends proximally beyond the open first end of the tubular member. This feature facilitates the application and removal of the present system to the limb to be treated.

The elongated hollow element is preferably seamless to better provide an effective sterile barrier. For example, this element can be derived from seamless tube stock or the like which itself is produced by conventional processing, e.g., extrusion or the like.

It is important that the elongated hollow element be substantially microbially impermeable. This feature allows the elongated hollow element to act as a sterile barrier between the limb being placed in traction, e.g., and being operated upon, and the surrounding atmosphere. In one embodiment, this element is preferably gas permeable which allows the limb being treated to have its external surface exposed to oxygen and/or other gases. This reduces any detrimental effects caused by confining the limb in the present system.

The elongated hollow element preferably does not contract around the limb being treated in response to the application of a traction or pulling force in a manner similar to the tubular member. Thus, these two components, i.e., the tubular member and the hollow element, are preferably of different constructions. However, as set forth herein, such components compliment each other and together produce substantial advantages. An additional embodiment involves the use of a combined tubular member/hollow element component which has substantially a single sidewall and which both contracts around the limb upon the application of a traction or pulling force and is substantially microbially impermeable. However, the expense of producing such a combined component may not warrant its use, particularly when a system employing two separate, relatively inexpensive components is very useful.

The elongated hollow element may be made of any suitable material or combination of materials, provided that this element functions as described herein. In one embodiment, the hollow element is preferably made of polymeric material, e.g., thermoplastic polymeric material. Examples of useful materials from which this element can be made include polyolefins, fluorinated polyolefins and the like and mixtures thereof. One specific material useful to make the elongated hollow element is expanded polytetrafluoroethylene, such as a product sold under the trademark Gore-tex, by W. L. Gore & Associates, Inc. Because of its beneficial combination of usefulness, availability and low cost, polyethylene is a particularly useful material from which to construct the hollow elongated element.

The elongated tubular member and elongated hollow element are preferably secured or held together at the least point, for example at or near the second end of the elongated tubular member. This securement can be done by clamping the two components together, adhesively securing these two components together and/or using some other securing technique. Such securing is beneficial so that the entire system can function together, e.g., to achieve substantial advantages. Preferably, the tubular member and hollow element are secured together in a manner so as not to compromise the integrity of the hollow element. For example, it is preferred that the tubular member and hollow element not be stitched together.

The attachment means may be of any suitable construction, provided that it functions as described herein. In a useful embodiment, the attachment means includes a loop secured to the elongated tubular member at or near the second end of the tubular member. A hook, e.g., an S-hook or the like, may be included. This hook is located on the loop and is sized and adapted to be connected directly to the raction force system.

In a particularly useful embodiment, the present system further includes a clamp means, e.g., a hog rings clamp or the like, acting to secure the hollow element and/or the attachment means, e.g., the loop of the attachment means, to the tubular member. Preferably, the clamp means acts to secure both the attachment means and the hollow element to the tubular member. In one particularly useful construction, the loop of the attachment means includes a knot which is located within the tubular member, preferably near the second end of the tubular member. The clamp means is placed around the tubular member distally of the knot and acts to hold the knot in place so that the loop can not be withdrawn from the second end of the tubular member.

The system may further include a cover, e.g., of tubular configuration, sized and adapted to be placed over the clamp and a portion of the elongated tubular member at or near the second end of the tubular member. Preferably, the cover is located over the second end of the tubular member. The attachment means, e.g., at least a portion of the loop and the hook described above, preferably extends distally from the cover. Although the cover may act to assist in holding the other components of the system together, its primary purpose is to make the appearance of the system more attractive. In one particularly useful embodiment, the cover is made from heat shrink material, e.g., material which compacts or shrinks upon the application of heat. Many heat shrink materials, in particular heat shrink polymeric materials such as polytetrafluoroethylene or the like, are conventional and well known in the art. During production of one particular embodiment of the present system, the heat shrink cover, in its expanded form, is placed over the second end of the tubular member, the clamp and the knot of the loop. Heat is then applied to the cover to cause the cover to shrink around these components.

A cushion means may be provided which is sized and adapted to be placed on, e.g., around, a portion of the patient's limb. This cushion means acts to cushion that portion of the limb against the direct or full impact to the traction force being applied to the limb. For example, when the limb being treated is a human arm, a wrist cushion may be included to protect the patient's wrist against the full impact of the traction force applied to the arm. This cushion means can be made of any suitable material, for example, resilient foamed polymeric material, cotton or the like. The cushion means can be separate from the other components of the system and placed on the patient's limb prior to placing the patient's limb into the tubular member/hollow element combination. Alternately, the cushion means can be adhesively secured to the inner wall(s) of the tubular member and/or hollow element. As a further alternative, the cushion means can be secured to a separate piece of tube stock which is held in place by the clamp means.

The present system is useful in a method of applying a traction force, e.g., during surgery, from a traction force system to a limb of a patient. In general, this method comprises placing at least a portion of the limb to be treated into an elongated tubular member/elongated hollow element combination, e.g., as described herein, through the open first end of the tubular member and the open end of the hollow element. A traction force from the traction force system is applied to the second end of the elongated tubular member. Preferably, a bandage is wrapped around the limb and the tubular member to secure the position of the limb relative to the tubular member.

The preferred construction of the present system allows for disposal after a single use. Thus, there is no need for repeated sterilizations and possible contamination between patients. The present system is preferably disposable and yet is a cost effective approach to applying traction, particularly on a short term basis such as during surgery.

These and other aspects and advantages of the present invention are set forth in the following detailed description and claims, particularly when considered in conjunction with the accompanying drawings in which like parts bear like reference numerals.

BRIEF DESCRIPTION OF THE DRAWINGS

FIG. 1 is a schematic view, in perspective, showing an embodiment of the present system as a surgical drape applied to the arm of a patient positioned for arthroscopic shoulder surgery.

FIG. 2 is an exploded view, in perspective, of certain components of the embodiment shown in FIG. 1.

FIG. 3 is a top front view, in perspective, showing the components shown in FIG. 2 in a ready-for-use condition.

FIG. 4 is a side view, partly in cross-section, showing the components shown in FIG. 2 with a human arm inserted.

FIG. 4A in an enlarged fragmentary side view, partly in cross-section, showing certain of the components assembled as in FIG. 4.

FIG. 5 is a cross-section view taken along line 5—5 of FIG. 4.

DETAILED DESCRIPTION OF THE DRAWINGS

Referring to the drawings, the present system as a surgical drape is shown generally at 10 and includes tubular sheet 12, braided tube 14, clamp 16, top cover 18, loop 20, S-hook 22, elastic bandage 24 and cushion ring 25.

Tubular sheet 12 has a first open end 28, a sidewall 30 and a second end 32. Sidewall 30 of tubular sheet 12, made of a polymeric material such as polyethylene or the like, is microbially impermeable so as to form a sterile barrier between the forward portion of the arm 26 being operated on and the surrounding environment. However, sidewall 30 of tubular sheet 12 is permeable to gases and thus, allows oxygen to come into contact with arm 26 within sidewall 30. Tubular sheet 12 is seamless and can be made from readily available polymeric material tube stock. Although it is most convenient and cost effective in producing surgical drape 10 that second end 32 of tubular sheet 14 be open, this is not necessary. Second end 32 can be closed. In any event, the interior space 34 defined by sidewall 30 is of sufficient size to receive a substantial portion of arm 26, as shown in FIG. 4.

Braided tube 14 includes a first open end 36, a braided sidewall 38 and a second open end 40. Braided sidewall 38 of braided tube 14, made of braids of polyester monofilaments, is porous and contracts in response to a pulling force being applied to second open end 40. Braided tube 14 may be envisioned as being constructed in a manner similar to a "Chinese Finger Trap", although much bigger to accommodate arm 26, as discussed hereinafter. A particularly useful polyester from which braided tube 14 can be made is sold by DuPont under the trademark Dacron.

Braided tube 14 can be fabricated by appropriately cutting a portion from a long length of tube stock. First and second open ends 36 and 40 are preferably treated, e.g., with adhesive or bonding agent, by heating or the like, to inhibit the individual strands or braids making up braided tube 14 from separating, unraveling and/or otherwise disadvantageously reducing the structural integrity of the braided tube 14. The sidewall 38 of braided tube 14 is seamless but, contrary to the sidewall 30 of the tubular sheet 12, is porous and permeable to microbes.

In the embodiment shown, the distal portion of tubular sheet 12 is placed inside the space 42 defined by sidewall 38 of braided tube 14. A reverse construction, i.e., with braided tube 14 inside the space 34 defined by sidewall 30 of tubular sheet 12, may also be used. However, the illustrated construction provides certain advantages. For example, the relatively more strong and tear resistant braided tube 14 acts to protect the tubular sheet 12, e.g., against accidental scalpel cuts during surgery. This helps to maintain the integrity of the sterile barrier formed by the tubular sheet 12. In addition, with the tubular sheet 12 between the braided tube 14 and the arm 26, the tubular sheet 12 acts as a cushion for arm 26 against the contracting force of braided tube 14.

As shown best in FIG. 3, tubular sheet 12 is sized to extend proximally beyond the first open end 36 of braided tube 14. Such extension facilitates the application and removal of the surgical drape 10 to and from the limb, e.g., arm 26. The length of this extension varies depending on the specific application and the specific limb involved. For example, the length of extension can vary in the range of about 0.5 inch or less to about 5 inches or more. If the surgical drape 10 is to be used on arm 26, the extension length preferably is in the range of about 1 inch to about 3 inches, in particular about 1.5 inches. These extension lengths are measured with surgical drape 10 in place on the limb, e.g., arm 26.

The tubular sheet 12 and braided tube 14, in particular the distal end portions 44 and 46 of tubular sheet 12 and braided tube 14, respectively, may be configured, e.g., tapered, to more closely approximate the shape of arm 26. However, this is not necessary and, because of cost and fabrication considerations, it is preferred that no such special shaping be involved. Of course, the tubular sheet 12 and braided tube 14 each is to be sized and shaped to perform as described herein.

Clamp 16, e.g., a conventional hog rings clamp, is positioned so as to hold the distal end portions 44 and 46 of tubular sheet 12 and braided tube 14, respectively, together. If desired, these distal end portions 44 and 46 may be adhesively secured together, e.g., using a conventional adhesive. In any event, tubular sheet 12 and braided tube 14 are secured together, preferably at the distal end portions 44 and 46. Clamp 16 performs another function, it secures loop 20 to braided tube 14.

A knot 50 is placed in loop 20, which can conveniently be made of nylon cord or the like. During fabrication of surgical drape 10, knot 50 is placed through second end 40 of braided tube 14 into space 42. The remainder of loop 20 extends distally from the braided tube 14. With knot 50 in space 42, clamp 16 is placed around the distal end portions 44 and 46 of tubular sheet 12 and braided tube 14, respectively, thus trapping knot 50 in space 42 and, thereby, securing loop 20 to braided tube 14.

S-hook 22, e.g., of conventional construction, is placed on loop 20 and acts as the direct link between surgical drape 10 and the traction system, shown generally at 52. Thus, the string-like element 54 which is attached to traction weights 56 is secured to S-hook 22 when surgical drape 10 is used to apply traction force to arm 26.

Cover 18 is hollow, tubular and made of conventional heat shrink polymeric material. During fabrication of surgical drape 10, after clamp 16 is placed to trap knot 50, as described above, cover 18, in its expanded state, is placed around clamp 16 and the distal end portions 44 and 46 of tubular sheet 12 and braided tube 14, respectively. Heat is then applied to cover 18 to cause cover 18 to shrink and assume a configuration as shown in FIG. 3. The primary purpose of cover 18 is to provide an attractive appearance to surgical drape 10, and it also may act to assist in maintaining the other components in proper position.

Bandage 24, e.g., a conventional elastic, self-adhering bandage, is wrapped around the tubular sheet/braided tube combination, as shown in FIG. 1, to hold surgical drape 10 securely in place relative to arm 26. Cushion ring 25, made of conventional foamed rubber, is placed around the patient's wrist, as shown in FIG. 4. Cushion ring 25 acts to protect the patient's wrist against the full impact of the traction force applied to arm 26.

Surgical drape 10 functions as follows. Various components of surgical drape 10 are assembled as described above and are as shown in FIG. 3. After positioning cushion ring 25 on the patient's wrist, this assembly is then placed on arm 26 by passing arm 26 into tubular sheet 12 and braided tube 14 to the extent desired. Bandage 24 is wrapped around the tubular sheet/braided tube combination, as shown in FIG. 1 to reduce the amount of movement of surgical drape 10 relative to arm 26. String-like element 54 is then attached to S-hook 22. This causes a traction force, from traction force system 52, to be applied to arm 26. Because of the unique construction of surgical drape 10, braided tube 14 contracts around arm 26 in a substantially uniform manner so that the traction force is distributed substantially uniformly over a relatively large area of arm 26. This protects arm 26, and in particular relatively small areas of arm 26, such as the fingers, from being damaged by the application of traction forces which may be excessive for such relatively small areas.

In addition, since the tubular sheet 12 is microbially impermeable, a sterile barrier between the arm 26 in surgical drape 10 and the surrounding environment is maintained. Thus, during surgery arm 26 may be moved into contact with other portions of the patient's body and/or surgical personnel may be required to maneuver arm 26. Using the present system, this can be accomplished without breaking the surgical sterile field.

After use, the string-like element 54 is removed from S-hook 22, bandage 24 is removed from around the tubular sheet/braided tubular combination and arm 26, and arm 26 is withdrawn from this combination. All components of surgical drape 10 are then disposed of.

While the present invention has been described with respect to various specific examples and embodiments, it is to be understood that the present invention is not limited thereto and that it can be variously practiced within the scope of the following claims.

We claim:

1. An apparatus useful for applying a traction force from a traction force system to a limb of a patient comprising:

an elongated tubular seamless member having an open first end and an opposing second end, sized and adapted to receive a substantial portion of a limb of a patient through said open first open, and being constructed so that the traction force from the traction force system is applied substantially uniformly over and substantially around at least a portion of the received limb;

an elongated seamless hollow element having an open end and a sidewall which is microbially impermeable, sized and adapted to receive the received limb through said open end; and attachment means secured to said elongated tubular member and acting to connect said elongated tubular member to the traction force system.

2. The apparatus of claim 1 which further comprises bandage means acting to secure the position of the received limb relative to said elongated tubular member.

3. The apparatus of claim 1 wherein said open end of said elongated hollow element extends proximally beyond said open first end of said elongated tubular member.

4. The apparatus of claim 1 wherein at least a portion of said elongated hollow element is substantially surrounded by said elongated tubular member.

5. The apparatus of claim 1 wherein said elongated tubular member is made of a braided material.

6. The apparatus of claim 1 wherein said elongated tubular member includes a porous sidewall and has a different construction than said elongated hollow element.

7. The apparatus of claim 1 wherein said elongated tubular member is made of braided monofilament fibers.

8. The apparatus of claim 1 wherein said elongated tubular member is made of polyester.

9. The apparatus of claim 1 wherein said elongated tubular member includes a sidewall which is seamless.

10. The apparatus of claim 1 wherein said sidewall of said elongated hollow element is seamless 11. The apparatus of claim 1 wherein said sidewall of said elongated hollow element is gas permeable.

12. The apparatus of claim 1 wherein said elongated hollow element has reduced tear strength relative to said elongated tubular member.

13. The apparatus of claim 1 wherein said elongated hollow element is made of polymeric material.

14. The apparatus of claim 1 wherein said elongated hollow element is made of a material selected from the group consisting of polyolefins, fluorinated polyolefins and mixtures thereof.

15. The apparatus of claim 1 wherein said elongated hollow element is made of polyethylene.

16. The apparatus of claim 1 wherein said elongated tubular member and said elongated hollow element are secured together at or near said second end of said elongated tubular members.

17. The apparatus of claim 16 which further comprises clamp means acting to secure said elongated tubular member and said elongated hollow element together.

18. The apparatus of claim 1 wherein said attachment means includes a loop secured to said elongated tubular member at or near said second end of said elongated tubular member.

19. The apparatus of claim 18 which further comprises clamp means acting to secure said loop to said elongated tubular members.

20. The apparatus of claim 19 wherein said clamp means further acts to secure said elongated tubular member to said elongated hollow element.

21. The apparatus of claim 19 wherein said loop extends out from said second end of said elongated tubular member.

22. The apparatus of claim 21 wherein said loop includes a knot located within said elongated tubular member.

23. The apparatus of claim 19 which further comprises a cover sized and adapted to be placed over said clamp means and said second end of said elongated tubular member.

24. The apparatus of claim 23 wherein said cover is made of heat shrink material.

25. The apparatus of claim 18 wherein said attachment means further includes a hook located on said loop, and sized and adapted to be connected directly to the traction force system.

26. The apparatus of claim 1 which further comprises a cushion means sized and adapted to be placed on a portion of the limb of the patient to cushion that portion of the limb against the full impact of the traction force.

27. A method of applying a traction force from a traction force system to a limb of a patient comprising:
placing at least a portion of a limb of a patient into an elongated seamless tubular member having an open first end and an opposing second end through said open first end, and into an elongated seamless hollow element having an open end and a sidewall which is microbially impermeable through said open end, said elongated tubular member being constructed so that the traction force from the traction force system is applied substantially uniformly over and substantially around at least a portion of said limb in said elongated tubular member; and
applying the traction force from the traction force system to said elongated tubular member.

28. The method of claim 27 which further comprises wrapping a bandage around at least a portion of said limb in said elongated tubular member to secure the position of said limb relative to said elongated tubular member.

29. The method of claim 27 wherein said open end of said elongated hollow extends proximally beyond said open first end of said elongated tubular member.

30. The method of claim 27 wherein at least a portion of said elongated hollow element is substantially surrounded by said elongated tubular member.

31. The method of claim 27 wherein said elongated tubular member is made of braided monofilament fibers.

32. The method of claim 27 wherein said limb is a human arm.

33. A surgical drape for protectively covering at least a portion of a limb of a patient while applying a traction force from a traction force system to the limb comprising:
an elongated seamless tubular member having a porous sidewall, an open first end and an opposing second end, sized and adapted to receive a limb of a patient through said open first end, and being constructed so that the traction force from the traction force system is applied substantially uniformly over and substantially around at least a portion of the received limb;
an elongated seamless hollow element having an open end and a sidewall which is microbially impermeable, sized and adapted to receive the received limb through said open end and being substantially surrounded by said elongated tubular member with said open end extending proximally of said open first end of said elongated tubular member;
bandage means acting to secure the position of the received limb relative to said elongated tubular member; and
attachment means secured to said elongated tubular member at or near said second end and acting to connect said elongated tubular member to the traction force system.

34. An apparatus useful for applying a traction force from a traction force system to a limb of a patient comprising:
an elongated member constructed as a Chinese finger trap and having an open first end and a opposing second end, sized and adapted to receive a substantial portion of a limb of a patient through said open first end, said elongated member being adapted so as to contract around at least a portion of the received limb upon the application of a traction force to said elongated member;
an elongated seamless hollow element having an open end and a sidewall which is microbially impermeable, sized and adapted to receive the received limb through said open end; and
attachment means secured to said elongated member and acting to connect said member to the traction force system.

35. The apparatus of claim 34 wherein said elongated hollow element is substantially surrounded by said elongated member.

* * * * *

UNITED STATES PATENT AND TRADEMARK OFFICE
CERTIFICATE OF CORRECTION

PATENT NO. : 4,966,167
DATED : October 30, 1990
INVENTOR(S) : Randall W. Jacobs, R. H. Peterson It is certified that error appears in the above-identified patent and that said Letters Patent is hereby corrected as shown below:

Col. 1, line 29, delete "Casperi" and insert -- Caspari --

Col. 1, line 38, delete "Casperi" and insert -- Caspari --

Col. 8, line 28, after "first" delete -- open -- and insert -- end --

Signed and Sealed this

Ninth Day of February, 1993

Attest:

STEPHEN G. KUNIN

Attesting Officer

Acting Commissioner of Patents and Trademarks